United States Patent
Wampole, Sr.

(10) Patent No.: US 7,179,327 B2
(45) Date of Patent: *Feb. 20, 2007

(54) WOOD TREATMENT PROCESS AND CHEMICAL COMPOSITION

(76) Inventor: Glenn P. Wampole, Sr., 119 Dartmoor Dr., Greer, SC (US) 29650

( * ) Notice: Subject to any disclaimer, the term of this patent is extended or adjusted under 35 U.S.C. 154(b) by 0 days.

This patent is subject to a terminal disclaimer.

(21) Appl. No.: 10/535,044

(22) PCT Filed: Nov. 20, 2002

(86) PCT No.: PCT/US02/37065

§ 371 (c)(1),
(2), (4) Date: Jan. 9, 2006

(87) PCT Pub. No.: WO2004/047539

PCT Pub. Date: Jun. 10, 2004

(65) Prior Publication Data

US 2006/0127689 A1    Jun. 15, 2006

Related U.S. Application Data

(63) Continuation-in-part of application No. 09/788,018, filed on Feb. 20, 2001, now Pat. No. 6,537,357.

(51) Int. Cl.
*A01N 59/12* (2006.01)
*B05D 7/06* (2006.01)
*B27K 3/34* (2006.01)

(52) U.S. Cl. .............. 106/18.35; 106/15.05; 424/667; 427/297; 427/397; 427/421.1; 427/428.01; 427/429; 427/440; 428/541

(58) Field of Classification Search ............. 106/15.05, 106/18.35; 424/667; 427/297, 397, 421, 427/428, 429, 440, 428.01, 421.1; 428/537.1, 428/541

See application file for complete search history.

(56) References Cited

U.S. PATENT DOCUMENTS

| | | |
|---|---|---|
| 3,775,047 A | 11/1973 | Weston |
| 3,985,921 A | 10/1976 | Rowell et al. |
| 4,329,383 A | 5/1982 | Joh |
| 4,780,341 A | 10/1988 | Chow |
| 4,804,384 A | 2/1989 | Rowell et al. |
| 5,470,614 A | 11/1995 | Chen et al. |
| 5,910,503 A | 6/1999 | Mattox et al. |
| 6,008,238 A | 12/1999 | el A'mma et al |
| 6,428,902 B1 | 8/2002 | Amundson et al. |
| 6,537,357 B2 | 3/2003 | Wampole, Sr. |
| 2002/0146465 A1 | 10/2002 | Lloyd et al. |

FOREIGN PATENT DOCUMENTS

| | | |
|---|---|---|
| JP | 56-47571 | 4/1981 |
| WO | WO 2004/047539 | 6/2004 |

OTHER PUBLICATIONS

Chen et al, "Fungal and Termite Resistance of Wood Reacted With Periodic Acid or Sodium, Periodate", Wood and Fiber Science, 21(2). 1989, pp. 163-168 (no month).
Derwent Abstract No. 1978-37092A, abstract of Japanese Patent Specifcation No. 53-039127 (Apr. 1978).
US Receiving Office, International Search Report, PCT/US02/37065, Feb. 11, 2003, 3 pages.

*Primary Examiner*—Anthony J. Green
(74) *Attorney, Agent, or Firm*—J Bennett Mullinax, LLC

(57) ABSTRACT

Treatment and preservation of wood, wood fiber products, and porous surfaces with a stabilized solution of periodic acid or iodic acid is provided.

7 Claims, No Drawings

WOOD TREATMENT PROCESS AND CHEMICAL COMPOSITION

RELATED APPLICATIONS

This application is a continuation-in-part of U.S. application Ser. No. 09/788,018, filed on Feb. 20, 2001 now U.S. Pat. No. 6,537,357, incorporated herein by reference, and is a National Entry under 35 USC §371 of Application No. PCT/US2002/037065 filed on 20 Nov. 2002.

FIELD OF THE INVENTION

This invention is directed towards a process and chemical composition for treating wood and similar porous surfaces so as to render the wood resistant to termites, mold, other fungi, and bacteria. The invention also relates to an improved chemical composition useful for imparting to wood resistance against termites, fungus, and bacterial organisms.

BACKGROUND OF THE INVENTION

This invention relates to a process and a chemical composition useful in the preservation of wood and wood fiber products against damage caused by insects such as termites, as well as other destructive organisms including fungus and bacteria. A variety of techniques are known in the art directed to the preservation of wood and wood-containing products.

For instance, a physical barrier such as paint may be applied to the surface of the wood to prevent injury or attack by a destructive organism. However, a paint barrier is not suitable to use as an extended barrier for wood surfaces which are in contact with the soil. Additionally, painted wood surfaces may lack the durability needed for extreme environmental conditions such as an outdoor deck material.

Other wood preservatives have included solid based applications of various toxins designed to kill organisms that may attack the treated wood. In particular, the use of aqueous salt compounds such as chromated copper arsenate (CCA) has been widely used in the pressure treated lumber industry. However, the use of toxic compounds and aqueous salt compounds has been linked to environmental concerns related to the contamination of the environment as salts of heavy metals and/or other toxic compounds are leached into the surrounding soil and water.

In addition to the environmental concerns brought about by the use of heavy metal salts and/or other wood preserving toxins, the leaching of materials from the wood lessens the resistance of the wood to decay. As such, over time, the treated wood may become less resistant to decay as the preservatives leach into the environment.

A variety of wood preservative techniques, chemicals, and related technology may be found in reference to the following U.S. patents and which are incorporated herein by reference.

| U.S. Patent Documents | | |
|---|---|---|
| 3775047 | November, 1973 | Weston 8/37 |
| 3985921 | October, 1976 | Rowell et al 427/317I |
| 4329383 | May, 1982 | Joh 428/36 |
| 4780341 | October, 1988 | Chow 427/440 |

| U.S. Patent Documents | | |
|---|---|---|
| 4804384 | February, 1998 | Rowell et al 8/181 |
| 5470614 | November, 1995 | Chin et al 427/440 |

Accordingly, there remains room for improvement and variation in the art with respect to processes and chemicals used in the treatment of wood products.

SUMMARY OF THE INVENTION

It is one aspect of at least one of the present embodiments to provide a treatment process for wood which renders the wood resistant to decay.

It is another aspect of at least one of the present embodiments to provide a chemical composition for use in wood treatment which provides a treated wood product in which the preservative agent does not substantially leach or migrate from the treated wood.

It is yet another aspect of at least one of the present embodiments to provide a chemical treatment composition for use with wood, wood products, and other porous substrates and which forms a substantially insoluble matrix within the substrate and protects the substrate against decay from biological agents or from moisture.

One suitable process of treating wood with a preservative comprises providing a wood substrate; applying to the wood substrate an aqueous solution comprising about 0.5% to about 50% by weight of an iodic acid, a periodic acid, or a combination thereof; about 0.05% to about 10% by weight of a fluorinated surfactant with a perfluorinated chain; and, optionally, an effective stabilizing amount of an ethoxylated nonylphenol; wherein the aqueous solution reacts with the wood substrate to form an insoluble iodine matrix within the wood substrate, the iodine matrix providing a moisture resistant barrier imparting to the wood preservative properties against termites and decay.

Another suitable wood preservative formulation may be provided by an aqueous solution comprising about 0.5% to about 50% by weight of an iodic acid, a periodic acid, or a combination thereof; about 0.05% to about 10% by weight of a fluorinated surfactant with a perfluorinated chain; and, optionally, an effective stabilizing amount of an ethoxylated nonylphenol. The formulation may be diluted with water or other aqueous-based liquid to provide a desired working solution.

These and other features, aspects, and advantages of the present invention will become better understood with reference to the following description and appended claims.

DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

As used herein, the term "decay" is used to describe a process of wood degradation that may occur from insects, such as termites, fungi, mold, and bacteria or degradation from a combination of these organisms or from exposure to excess moisture.

As used herein, the term "preservative", and variations thereof, include chemical compositions and treatments which provide resistance to decay.

The present invention provides a preservative useful in protecting wood, wood products, and other porous materials. Additionally, the preservative and process described herein also provides a water and moisture barrier to the treated surface. The preservative may be provided by a stabilized solution of iodic acid, a stabilized solution of periodic acid, or a stabilized mixture of iodic and periodic acid. Hereafter, the solution of iodic acid, periodic acid, or a blend of both iodic and periodic acids are referred to generally as a stablized iodine solution.

In accordance with this invention, it has been found that an aqueous solution of periodic and/or iodic acid provides a water soluble preservative useful for treating wood. When lumber, processed wood products, cellulosic products, or other porous materials such as natural or synthetic fabrics, are surface treated with the stabilized aqueous iodine solution, the iodine solution enters in to the substrate. The iodine present within the iodine solution is highly reactive with other materials, particularly with cellulose, lignin, and other organic constituents commonly found in wood and cellulosic containing products. While not wishing to be limited by theory, it is believed that either elemental iodine or an iodine reaction product is formed within the wood or other cellulose-containing substrate. The resulting reaction product has been found to be stable, i.e., resistant to leaching, and persists within the wood or cellulosic product without noticeable loss of initial treatment color or diminished effectiveness as a preservative.

When the applied surface/substrate is allowed to dry, an iodine reaction product or matrix is formed. The iodine matrix has been found to provide the substrate with resistance to decay and also limits water absorption. While not wishing to be limited by theory, it is Applicant's belief that the matrix material which forms from the iodine solution contains at least a portion of elemental iodine or other insoluble reaction product of iodine. The iodine matrix has been found to not leach from a treated wood substrate. Examination of treated surfaces reveal dense, plate-like formations which the inventor believes is, at least in part, comprised of elemental iodine. Irrespective of the theory, the resulting matrix is characterized as being a hardened material which is itself non-porous, is insoluble in water, provides water resistance with respect to the substrate, and provides resistance to decay.

Iodic acid and periodic acid solutions are highly reactive and will rapidly react and/or break down in the presence of a suitable reagent or substrate. In addition, exposure to light or high temperatures also results in the decomposition of liquid solutions of iodic and periodic acids. Because of these properties of iodic acid and periodic acid, solutions of these materials are not stable for long-term storage. In addition, it has been found that additives that may enhance the treatment of wood such as surfactants or emulsifiers will cause a degradation of the iodic or periodic acids. The high reactivity of the iodic or periodic acid solutions is one obstacle towards using iodic and periodic acid solutions for treatment of wood products on a commercial scale.

In accordance with one aspect of the present invention, it has been found that liquid solutions of periodic and iodic acid may be stabilized so as to provide an adequate shelf life such that liquid forms of the iodic and periodic acid may be used in the treatment of lumber, wood products, and other porous materials.

The ability to stabilize aqueous solutions of periodic and/or iodic acid are surprising given the highly reactive nature of the reagents. In an effort to increase penetration and coating of substrates, a variety of surfactants were evaluated to see if improvements in treatment protocols were noted. Most of the surfactants evaluated brought about undesired reactions with the iodine solutions and were, therefore, unsuitable for use in wood treatment formulations designed for long-term storage. However, it was found that a polyfluoro-sulfonic acid available as Forafac (R) 1033D from Atofina, Philadelphia, Pa. (USA), provided not only desirable surfactant properties but yielded the unexpected result of stabilizing the iodic and/or periodic solutions. In accordance with this invention, it has been found that the inclusion of the polyfluoro-sulfonic acid and/or fluorinated anionic surfactant will extend the shelf life of the iodic and/or periodic acid. It has been found that adding the fluorinated surfactant to a stock solution of iodic or periodic acid containing composition at a concentration of between about 0.1% to about 10% will provide improved solution stability as well as maintaining the desirable surfactant activity.

It has also been found beneficial to add an emulsifying agent to improve the treatment efficiency of the iodine containing preservative formulation. Again, a variety of commercially available emulsifiers were evaluated, most emulsifiers creating an undesired reaction with the iodic or periodic acid resulting in formulations having a short, unusable shelf life. However, an emulsifier available from Ethox Chemicals, Inc., Greenville, S.C. (USA), under the trade name Ethal NP-370 has been found to be effective and has been further found to improve solution stability for a concentrate. The NP-370 is a polyoxyethylene nonylphenyl ether. A 1.0% to about 7% addition of a 30 mole Ethal NP-370 to a concentrate has been found to provide suitable emulsifying properties while offering the unexpected advantage of improving the stability of the solution for a shelf life of at least three months.

Set forth below in Table 1 is a preferred exemplary embodiment of a stabilized iodine solution concentrate. The concentrate has been found to exhibit a shelf life of at least three months while maintaining the useful surfactant and emulsifying properties of the listed additives. The periodic acid may be obtained at a 50% concentration from Ajay North America, L.L.C., Powder Springs, Ga. (USA).

TABLE 1

| | (Concentrate) | | | |
| --- | --- | --- | --- | --- |
| Reagent | Vol. (gal) | lbs/gal | Batch Weight (lbs) | Weight (%) |
| Periodic Acid (50% concentration) | 60.853 | 14.7898 | 900 | 90.0 |

TABLE 1-continued (Concentrate)

| Reagent | Vol. (gal) | lbs/gal | Batch Weight (lbs) | Weight (%) |
|---|---|---|---|---|
| Forafac 1033D | 4.615 | 10.8342 | 50 | 5.0 |
| NP 370 (30 mole) | 5.660 | 8.8340 | 50 | 5.0 |

As set forth in Table 2, the concentrate solution of Table 1 may be diluted to a working concentration found useful for the surface treatment of wood and other cellulosic substrates. It is believed that the working solution concentration may vary depending upon the particular substrate being treated. More diluted or more concentrated working solutions are believed to also be effective. It has been found that the working solution may be sprayed, or applied with brush or roller to the surface of a wooden board. Additionally, the working solution may be applied to a wood or similar substrate by impregnating the wood under pressure with the working solution of the preservative formulation such as the one provided in Table 2. Any suitable pressure vessel may be employed. The actual process conditions would depend upon the species of wood being treated, the length and width of the wood, and other characteristics of the wood such as whether the wood has been air dried, kiln dried, etc. Within these process parameters, however, it is believed that a pressure of about 130 to about 150 psi for a treatment time of about 20 minutes to about 4 hours will suffice.

TABLE 2

(Exemplary Working Solution)

| Reagent | Vol. (gal) | lbs/gal | Batch Weight (lbs) | Weight (%) |
|---|---|---|---|---|
| Water | 991 | 8.334 | 8258.99 | 98.49% |
| *Periodic Acid (50% concentration) | 7.69 | 14.7898 | 113.87 | 1.36% |
| *Forafac 1033D | 0.584 | 10.8342 | 6.33 | 0.075 |
| *NP 370 (30 mole) | 0.717 | 8.8340 | 6.33 | 0.075 |

*as provided by the concentrate in Table 1

Following application of the wood preservative using any of the above techniques, the wood is preferably air dried at ambient temperature. Following drying, a sample of the wood may be cut and penetration of the formulation may be determined by visualization of the noted color change within the wood. If needed, the conditions of pressure and dwell time may be modified so as to achieve greater or lesser penetration of the wood with the preservative. In addition, the working solution may also be varied to provide for a more or a less concentrated working solution which would also affect the preservative qualities of the end product. As seen in reference to Table 2, given the low percentage of acid present within the working solution, it is believed that stronger working solutions may also be safely used to obtain either greater penetration or a higher level of the resulting iodine matrix within the wood and without adversely affecting the quality of the wood via any acidic degradation.

For instance, for marine or submerged applications, a more concentrated working solution along with more aggressive application techniques may be used to treat the wood products. In this manner, enhanced concentrations of the iodine matrix reaction product will occur and are believed to afford greater protection against biological degradation or water damage.

Upon application of the working solution, the surface of the board undergoes an immediate color change to a tan or tannish-orange color. The color change is believed to represent the rapid formation of an iodine reaction product which persists within the wood in a substantially insoluble form. The iodine reaction product is present within the wood or cellulose matrix and renders the wood resistant to decay. Further, the reaction product, while not providing a barrier surface to water and moisture, appears to limit moisture uptake and makes the substrate resistant to the deleterious effects of water and moisture which would otherwise occur on untreated wood.

It has also been observed that existing pressure treated wood such as CCA pressure treated wood may be subsequently surface treated with the stabilized iodine solution of the present invention. The presence of the CCA compounds does not interfere with the topical application of the stabilized iodine solution. A similar persistent color change as noted above occurs and persists in a substantially leach free manner.

Lengths of kiln-dried Southern pine 2×4s have had a preservative as set forth in Table 2 spray applied to the surface of the wood. Upon application to the wood, the wood immediately forms a tan or tannish-orange color which has been found to persist during subsequent two-year outdoor environmental exposure tests. Comparative control samples of commercially obtained CCA pressure treated lumber have exhibited surface mold growth under identical circumstances. Such mold growth has not been observed on the surface of the wood as treated by the present invention.

The compatibility of the stabilized iodine solution as a wood preservative with conventional CCA pressure treated wood has also been evaluated. In this instance, CCA pressure treated 4×4 posts had a portion of the posts additionally treated with a surface application of the stabilized iodine solution as set forth in Table 2. The stabilized iodine solution formed the characteristic color change as noted above and appears to be compatible with existing pressure treated wood. Following a two-year interval of environmental exposure, the portion of the post treated only with CCA exhibits a high level of surface mold and has undergone a characteristic weathering color loss. In contrast, adjacent sections of the post surface treated with the stabilized iodine solution as set forth in Table 1 has exhibited no surface mold growth. In addition, there has been no loss or degradation of the initial color.

The evaluations to date have indicated that the stabilized iodine solution provides for a treated wood product which is resistant to termites, fungi and mold, bacteria, and damage from moisture. The iodine matrix appears to render the surface and treated interior portions of the wood with an iodine-derived material which will not support the growth or maintenance of destructive organisms. Further, observations support the conclusion that the iodine matrix reaction products are substantially insoluble as noted by no loss of color or loss of decay resistance resistance over time. Accordingly, the wood preservative composition and the process of using the wood preservative composition offers numerous advantages over the currently available alternatives used for treating wood.

While it has not been verified, Applicant notes the possibility that the stabilized iodine treatment may interact favorably with conventional CCA pressure treated lumber so as to prevent or degrade leaching of CCA compounds from the wood. If demonstrated, the stabilized iodine solution could be used to advantage to surface treat existing CCA treated wood structures so as to minimize further leaching from the subsequently treated surfaces. In any event, the surface treatment with the iodine preservative is compatible with previously pressure treated wood and affords the surface of the wood enhanced protection against surface mold growth.

While the exemplary embodiment provided above uses periodic acid as the iodine source, it is believed that iodic acid may also be used in a similar manner. Likewise, combinations of iodic and periodic acid may also be employed.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. A process of treating wood with a preservative comprising:
   providing a wood substrate;
   applying to the wood substrate an aqueous solution comprising about 0.5% to about 50% of an iodic acid, a periodic acid, or a combination thereof;
   about 0.05% to about 10% of a fluorinated surfactant with a perfluorinated chain; and,
   optionally, an effective stabilizing amount of an ethoxylated nonylphenol;
   wherein said aqueous solution reacts with the wood substrate to form an insoluble iodine matrix within the wood substrate, said iodine matrix providing a moisture resistant barrier imparting to the wood preservative properties against termites and decay.

2. A preservative solution for cellulosic materials comprising:
   an aqueous solution comprising about 0.5% to about 50% of an iodic acid, a periodic acid, or a combination thereof;
   about 0.05% to about 10% of a fluorinated surfactant with a perfluorinated chain; and,
   optionally, an effective stabilizing amount of an ethoxylated nonylphenol.

3. The process according to claim 1 wherein said aqueous solution comprises about 0.5% to about 5.0% of an iodic acid, a periodic acid, or a combination thereof.

4. The process according to claim 1 where in said applying step is selected from the groups consisting of spraying, brushing, rolling, dipping, pressurization, and combinations thereof.

5. The product according to the process of claim 1.

6. A decay resistant wood product comprising a wooden substrate, said substrate having found therein an iodine matrix formed by the reaction between said wood substrate and a periodic acid containing an effective amount of a periodic acid stabilizer selected from the group consisting of fluorinated surfactants having a perfluorinated chain, ethoxylated nonylphenols, and combinations thereof.

7. The wood product according to claim 6 wherein said effective amount of said stabilizer comprises at least about 0.05% by weight.

* * * * *